(12) United States Patent
Liu et al.

(10) Patent No.: US 8,309,611 B2
(45) Date of Patent: Nov. 13, 2012

(54) METHODS AND COMPOSITIONS FOR TREATING LUNG CANCER

(75) Inventors: Sheng-Yung Liu, New Taipei (TW); San-Bao Hwang, New Taipei (TW); Wu-Che Wen, New Taipei (TW)

(73) Assignee: Golden Biotechnology Corporation, West Trenton, NJ (US)

( * ) Notice: Subject to any disclaimer, the term of this patent is extended or adjusted under 35 U.S.C. 154(b) by 0 days.

(21) Appl. No.: 13/070,308

(22) Filed: Mar. 23, 2011

(65) Prior Publication Data

US 2012/0071426 A1    Mar. 22, 2012

(51) Int. Cl.
*C07C 49/543* (2006.01)
*C07C 49/557* (2006.01)
*A61K 31/12* (2006.01)

(52) U.S. Cl. ........................... 514/690; 568/377

(58) Field of Classification Search ............ 514/690; 568/377
See application file for complete search history.

(56) References Cited

U.S. PATENT DOCUMENTS

| 7,342,137 | B1 | 3/2008 | Liu et al. | |
|---|---|---|---|---|
| 2004/0102527 | A1* | 5/2004 | Miyagawa et al. | 514/690 |
| 2011/0009494 | A1* | 1/2011 | Liu et al. | 514/690 |
| 2011/0059122 | A1* | 3/2011 | Liu et al. | 424/195.15 |
| 2011/0059123 | A1* | 3/2011 | Liu et al. | 424/195.15 |
| 2011/0060055 | A1* | 3/2011 | Liu et al. | 514/690 |
| 2011/0060056 | A1* | 3/2011 | Liu et al. | 514/690 |
| 2011/0060057 | A1* | 3/2011 | Liu et al. | 514/690 |
| 2011/0060058 | A1* | 3/2011 | Liu et al. | 514/690 |

FOREIGN PATENT DOCUMENTS

| CN | 101225066 | 7/2008 |
|---|---|---|
| GB | 2453808 | 4/2009 |
| WO | WO-2012-039793 | 3/2012 |

OTHER PUBLICATIONS

Chen and Yang, "New Steroid Acids from *Antrodia cinnamomea*, a Fungal Parasite of *Cinnamomum micranthum*," J Natural Products 58(11):1655-1661 (1995).
Cherng et al., "Triterpenoids from *Antrodia cinnamomea*," Phytochemistry 41(1):263-267 (1996).
Cherng and Chiang, "Three New Triterpenoids from *Antrodia cinnarnomea*," J Natural Products 58(3):365-371 (1995).
Chiang et al., "A Sesquiterpene Lactone, Phenyl and Biphenyl Compounds from *Antrodia cinnamomea*," Phytochemistry 39(3):613-616 (1995).
Yang et al., "Steroids and Triterpenoids of *Antrodia cinnamomea*—A Fungus Parasitic on *Cinnamomum micrantthum*," Phytochemistry 41(5):1389-1392 (1996).
Lee et al. "A New Cytotoxic Agent from Solid-State Fermented Mycelium of *Antrodia camphorata*." Planta Medica 2007, 73:1412-1415.
PCT/US2011/032785 International Search Report and Written Opinion mailed Feb. 27, 2012.
Yang et al. New Constituents with iNOS Inhibitory Activity from Mycelium of *Antrodia camphorata*. Planta Medica 2009, 75:512-516.

* cited by examiner

*Primary Examiner* — Brandon Fetterolf
*Assistant Examiner* — Anna Pagonakis
(74) *Attorney, Agent, or Firm* — Wilson, Sonsini, Goodrich & Rosati

(57) ABSTRACT

The present invention provides methods and compositions for treating lung cancer by cyclohexenone compounds.

25 Claims, 14 Drawing Sheets

Compound 1 Concentration (µg/ml)

0          0.1          0.3

Compound 1 Concentration (µg/ml)

0.6          1          3

Compound 1 Concentration (µg/ml)

0          0.1          0.3

Compound 1 Concentration (µg/ml)

0.6          1          3

METHODS AND COMPOSITIONS FOR TREATING LUNG CANCER

CROSS-REFERENCE

This application claims the benefit of Taiwan Application No. 099131844, filed Sep. 20, 2010, and Taiwan Application No. 099145853, filed Dec. 24, 2010, which applications are incorporated herein by reference.

BACKGROUND OF THE INVENTION

Lung cancer is a disease which consists of uncontrolled cell, growth in tissues of the lung. This growth may lead to metastasis, which is the invasion of adjacent tissue and infiltration beyond the lungs. The vast majority of primary lung cancers are carcinomas, derived from epithelial cells. Lung cancer, the most common cause of cancer-related death in men and women, is responsible for 1.3 million deaths worldwide annually, as of 2004.

The main types of lung cancer are small cell lung cancer (SCLC) and non-small cell lung cancer (NSCLC). Small cell lung cancer (SCLC) is a fast-growing type of lung cancer. It spreads much more quickly than non-small cell lung cancer. There are three different types of small cell lung cancer: small cell carcinoma (oat cell cancer), mixed small cell/large cell carcinoma and combined small cell carcinoma. Most small cell lung cancers are the oat cell type. Non-small cell lung cancer (NSCLC) is the most common type of lung cancer. There are three forms of NSCLC: adenocarcinomas, squamous cell carcinomas and large cell carcinomas. Adenocarcinomas are often found in an outer area of the lung. Squamous cell carcinomas are usually found in the center of the lung by an air tube (bronchus). Large cell carcinomas can occur in any part of the lung. They tend to grow and spread faster than the other two types.

Common treatments for lung cancer include palliative care, surgery, chemotherapy, and radiation therapy.

SUMMARY OF THE INVENTION

In one aspect provides herein for the treatment of lung cancer comprising administering to a subject a therapeutically effective amount of a cyclohexenone compound having the structure:

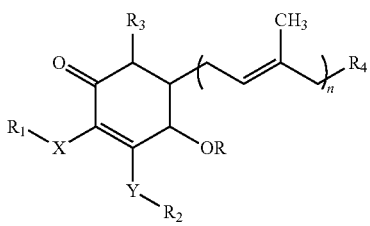

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In another aspect provides herein methods of treating or preventing a cell proliferative disorder of the lung, comprising administering to a subject in need a therapeutically effective amount of a cyclohcxenone compound having the structure:

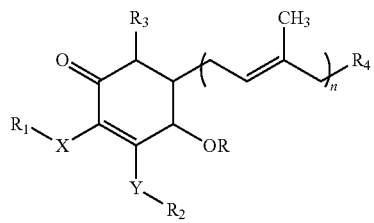

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In another aspect provides herein methods for inhibiting lung cancer cells comprising contacting said cancer cells a therapeutically effective amount of a cyclohexenone compound having the structure:

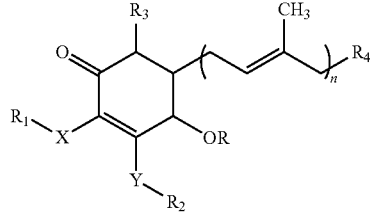

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)NR_5R_6$, halogen, 5 or 6, membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows cell viability rate of lung cancer cell lines A549, CL1-0, and CL1-5. FIG. 1B shows cell viability rate of lung cancer cell line DMS 114.

FIG. 2A shows dishes of the A549 colonies treated with 0, 0.1, 0.3, 0.6, 1 and 3 µg/ml of compound 1. FIG. 2B shows results of A549 colony forming ability (%) calculated by the number of 1 mm size colonies in each dish.

FIG. 3A shows dishes of the CL1-0 colonies treated with 0, 0.1, 0.3, 0.6, 1 and 3 µg/ml of compound 1. FIG. 3B shows results of CL1-0 colony forming ability (%) calculated by the number of 1 mm size colonies in each dish.

FIG. 4A shows dishes of the CL1-5 colonies treated with 0, 0.1, 0.3, 0.6, 1 and 3 µg/ml of compound 1. FIG. 4B shows results of CL1-5 colony forming ability (%) calculated by the number of 1 mm size colonies in each dish.

DETAILED DESCRIPTION OF THE INVENTION

Figure 1A:
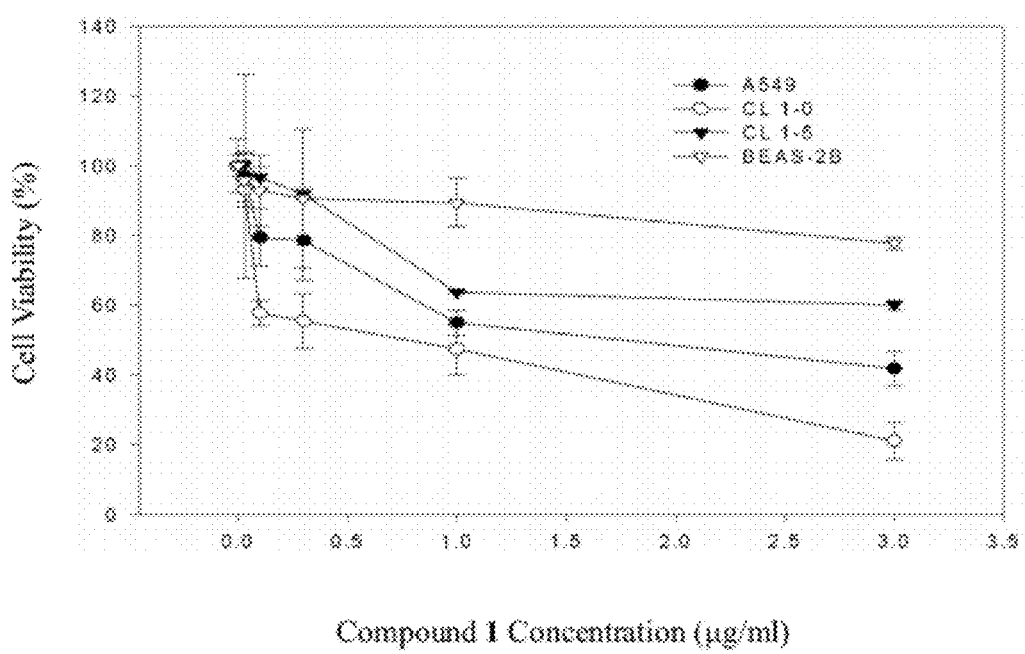
FIG. 1A-B show illustrative results of lung cancer cell viability treated with the exemplary cyclohexenone compound 1.

Common treatments for lung cancers (including relapsed and refractory lung cancers) include palliative care, surgery, chemotherapy, and radiation therapy. Many synthetic anti-canceragents used in chemotherapy cause discomfort or toxicity issues. The invention cyclohexenone compounds, in some embodiments, are obtained from extracts of natural products and provide reduced complications and/or side effects. Provided herein are methods for the treatment of lung cancer by administering a cyclohexenone compound provided herein to a subject (e.g. a human). The cyclohexenone compounds provide therapeutic benefit to a subject being treated for lung cancer or lung cancer cell proliferation (see Examples 1-7).

In some embodiments, there are provided methods for the treatment of lung cancer comprising administering to a subject a therapeutically effective amount of a cyclohexenone compound having the structure:

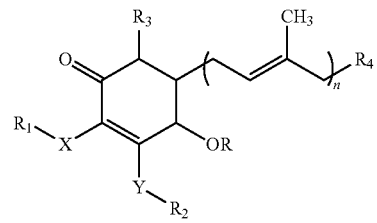

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$-$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the methods reduce lung cancer tumor size or tumor volume. In some embodiments, the methods decrease lung cancer tumor growth rate. In certain embodiments, the lung cancer is adenocarcinoma lung cancer, small cell lung cancer or non-small cell lung cancer. In some embodiments, the cyclohexenone compound induces cell death in the lung cancer. In certain embodiments, the cell death is apoptosis. In some embodiments, the subject is human. See Examples 2-7.

In some embodiments, the cyclohexenone compound having the structure

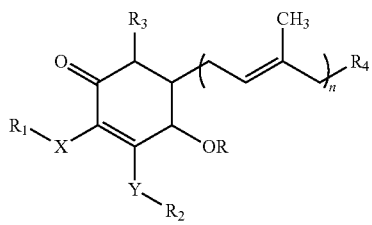

is prepared synthetically or semi-synthetically from any suitable starting material. In other embodiments, the cyclohexenone compound is prepared by fermentation, or the like. For example, Compound 1 (also known as Antroquinonol™ or "Antroq") or Compound 3, in some instances, is prepared from 4-hydroxy-2,3-dimethoxy-6-methylcyclohexa-2,5-dienone. The non-limited exemplary compounds are illustrated below.

1
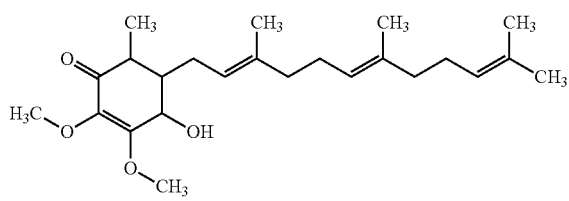

2
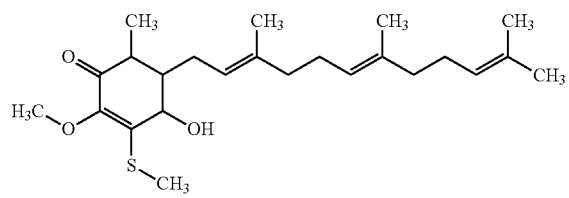

3
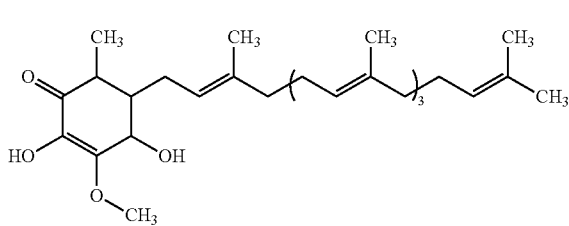

4
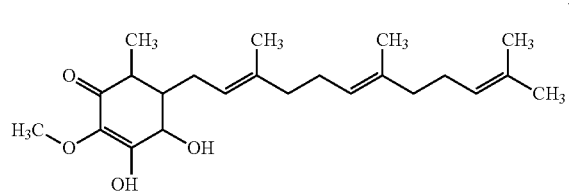

5
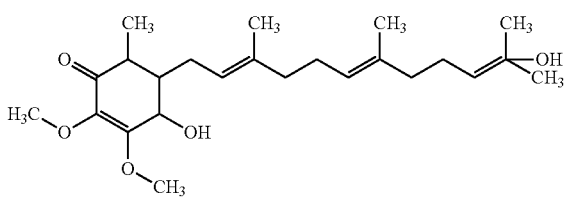

6
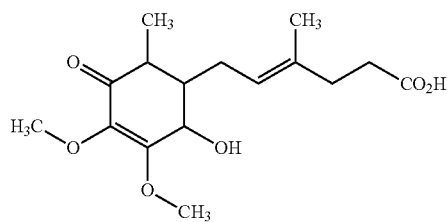

7
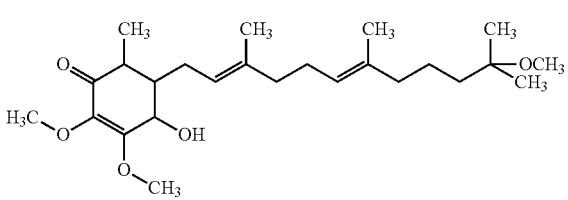

8
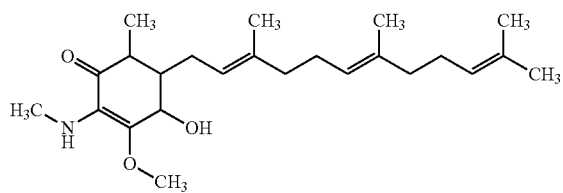

9
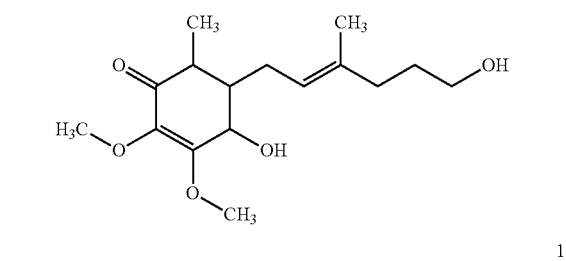

10
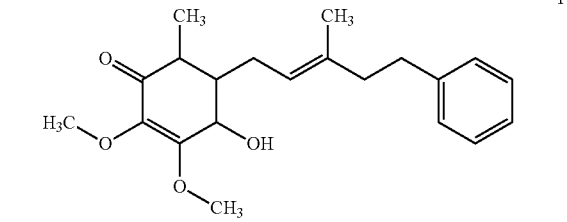

11
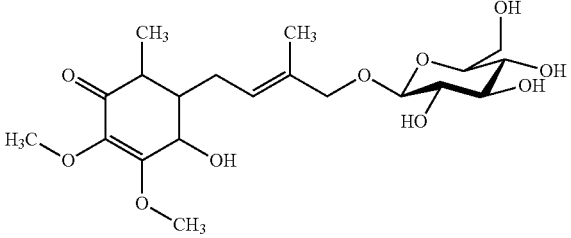

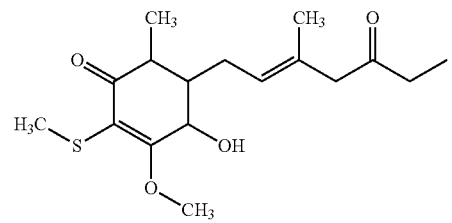

12

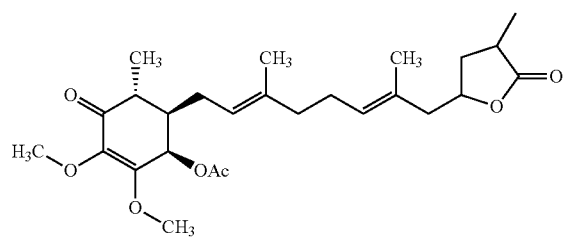

13

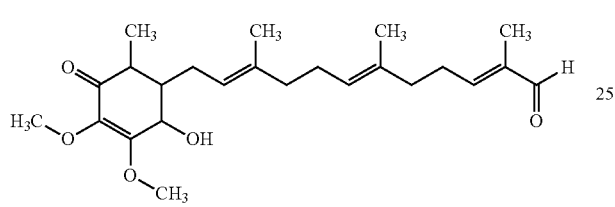

14

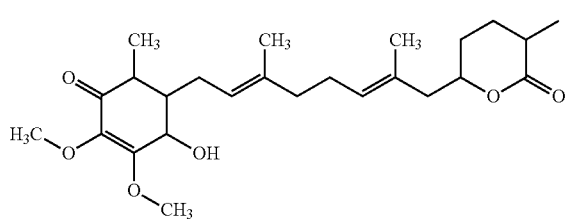

15

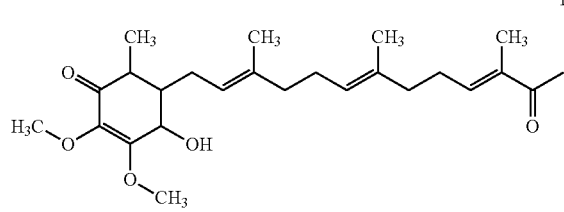

16

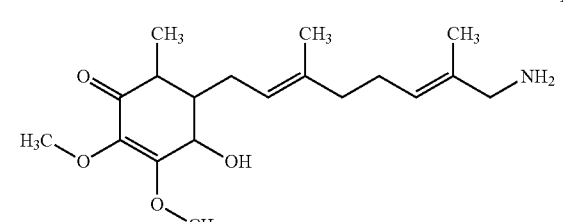

17

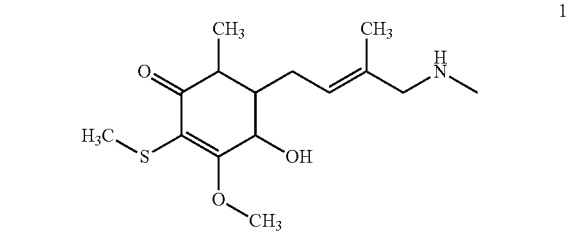

18

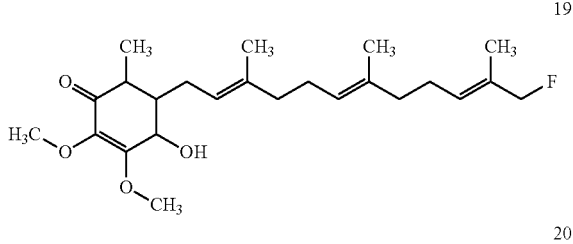

19

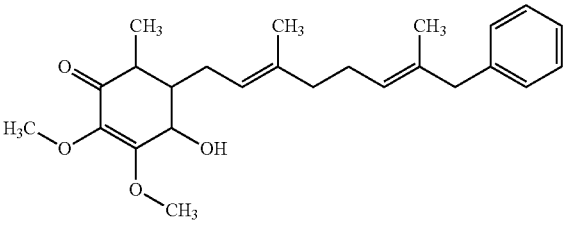

20

In other embodiments, the cyclohexenone compound having the structure

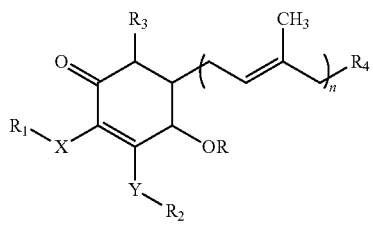

is isolated from the organic solvent extracts of *Antrodia camphorate*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, R is a hydrogen, $C(=O)C_3H_8$, $C(=O)C_2H_5$, or $C(=O)CH_3$. In some embodiments; $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, $C_2$-$C_8$alkenyl, $C_2$-$C_8$alkynyl, aryl, and glucosyl, wherein 5 or 6-membered lactone, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound is

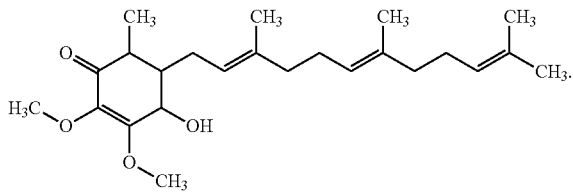

In some embodiments, there are provided methods of treating or preventing a cell proliferative disorder of the lung, comprising administering to a subject in need a therapeutically effective amount of a cyclohexenone compound having the structure:

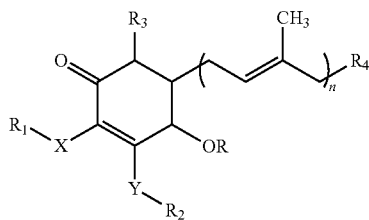

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_1$-$C_8$alkenyl, $C_1$-$C_8$alkynyl, aryl, glucosyl, wherein 5 or 6-membered lactone, $C_1$-$C_8$alkyl, $C_1$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the cell proliferative disorder of the lung is lung cancer. In certain embodiments, the cell proliferative disorder of the lung is a precancerous condition of the lung. In certain embodiments, the cell proliferative disorder of the lung is hyperplasia of the lung. In certain embodiments, the cell proliferative disorder of the lung is metaplasia of the lung. In some embodiments, the subject is human.

In some embodiments, the cyclohexenone compounds provided herein possess the therapeutic effects of inhibiting lung cancer cell proliferation. See Examples 2 and 3.

In some embodiments provide methods for inhibiting lung cancer cells comprising contacting said cancer cells a therapeutically effective amount of a cyclohexenone compound having the structure:

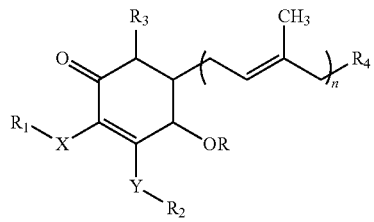

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl; $R_7$ is a $C_1$-$C_8$alkyl, $OR_5$ or $NR_5R_6$;

m=1-12; and n=1-12; or a pharmaceutically acceptable salt, metabolite, solvate or prodrug thereof. In some embodiments, the lung cancer cells comprise non-small cell lung cancer cells, small cell lung cancer cells or adenocarcinoma lung cancer cells. In some embodiments, the lung cancer cells are human lung cancer cells. In some embodiments, the lung cancer cells comprise lung cancer cell lines A549, NCI-H460, CL1-0, CL1-5, DMS 114, or the like. In certain embodiments, the lung cancer cells comprise lung cancer cell lines A549, NCI-H460, DMS 114, or the like.

In some embodiments, the cyclohexenone compounds provided herein possess the therapeutic effects of inhibiting lung cancer cell migration or invasion. See Example 4.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "$C_1$-$C_8$ alkyl" or similar designations. By way of example only, "$C_1$-$C_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$alkylene. In another aspect, an alkylene is a $C_1$-$C_8$alkylene. Typical alkylene groups include, but are not limited to, —$CH_2$—, —CH($CH_3$)—, —C($CH_3$)$_2$—, —$CH_2CH_2$—; —$CH_2CH(CH_3)$—, —$CH_2C(CH_3)_2$—, —$CH_2CH_2CH_2CH_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as hetcroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tctrahydropyranyl, dihydropyranyl, tetrahydrothiopyranyl, piperidinyl, morpholinyl, thiomorpholinyl, thioxanyl, piperazinyl, aziridinyl, azetidinyl, oxctanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentynyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkenyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butynyl, pentynyl, hexynyl, heptynyl, and the like.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

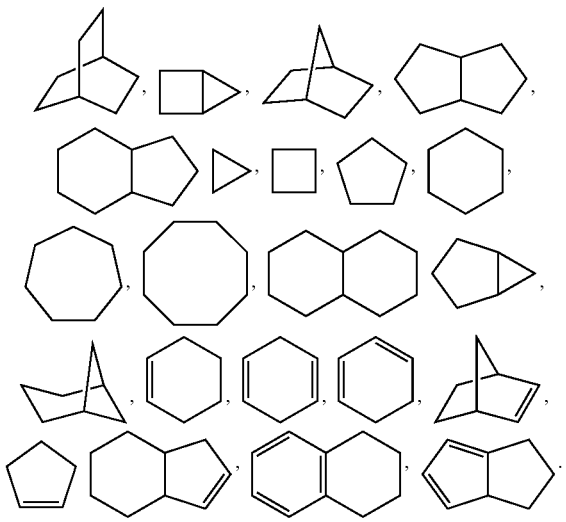

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "glucosyl" as used herein, include D- or L-form glucosyl groups, in which the glucosyl group is attached via any hydroxyl group on the glucose ring.

Certain Pharmaceutical and Medical Terminology

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot. Some of the species in this genus are have medicinal properties, and have been used in Taiwan as a Traditional medicine.

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

Pharmaceutical Composition/Formulation

In some embodiments provide compounds having the structure:

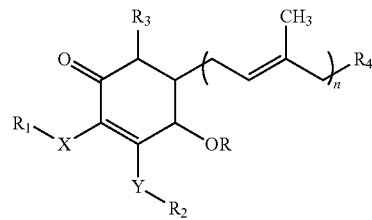

wherein each of X and Y independently is oxygen, $NR_5$ or sulfur;

R is a hydrogen or $C(=O)C_1-C_8$alkyl;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1-C_8$alkyl, $C_2-C_8$alkenyl, $C_2-C_8$alkynyl, aryl, glucosyl, wherein 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1-C_8$ alkyl, $C_2-C_8$ alkenyl, $C_2-C_8$ alkynyl, $C_3-C_8$ cycloalkyl, and $C_1-C_8$ haloalkyl;

each of $R_5$ and $R_6$ is independently a hydrogen or $C_1-C_8$alkyl;

$R_7$ is a $C_1-C_8$alkyl, $OR_5$ or $NR_5R_6$;

m=1-12; and n=1-12; or a pharmaceutically acceptable salt, metabolite, solvate or prodrug thereof.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In certain embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_2Ph$, $CH_2CH=C(CH_3)(CHO)$, $CH_2CH=C(CH_3)(C(=O)CH_3)$, 5 or 6-membered lactone, aryl, or glucosyl, wherein 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1-C_8$ alkyl, $C_2-C_8$ alkenyl, $C_2-C_8$ alkynyl, $C_3-C_8$ cycloalkyl, and $C_1-C_8$ haloalkyl. In certain embodiments, $R_4$ is $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein 5 or 6-membered lactone, aryl, and glucosyl are optionally substituted With one or more substituents selected from $NR_5R_6$, $OR_5$, $OC(=O)R_7$, $C(=O)OR_5$, $C(=O)R_5$, $C(=O)NR_5R_6$, $C_1-C_8$ alkyl, $C_2-C_8$ alkenyl, $C_2-C_8$ alkynyl, $C_3-C_8$ cycloalkyl, and $C_1-C_8$; haloalkyl.

In certain embodiments, the compound is selected from group consisting of
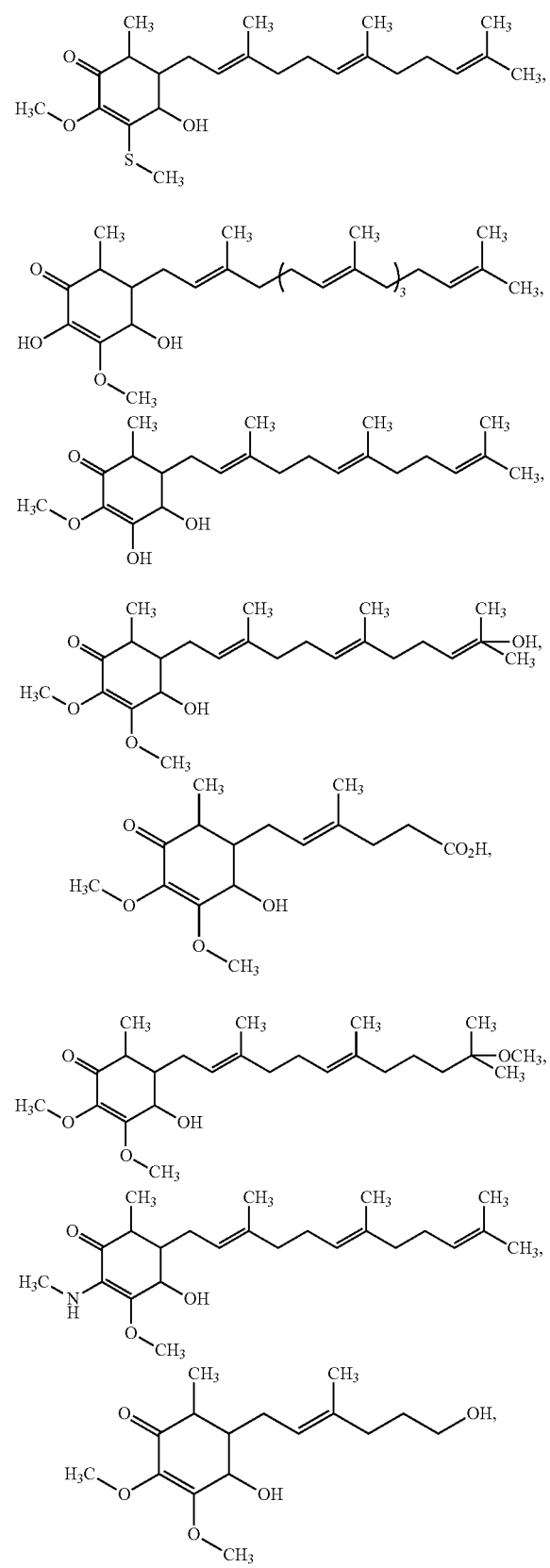
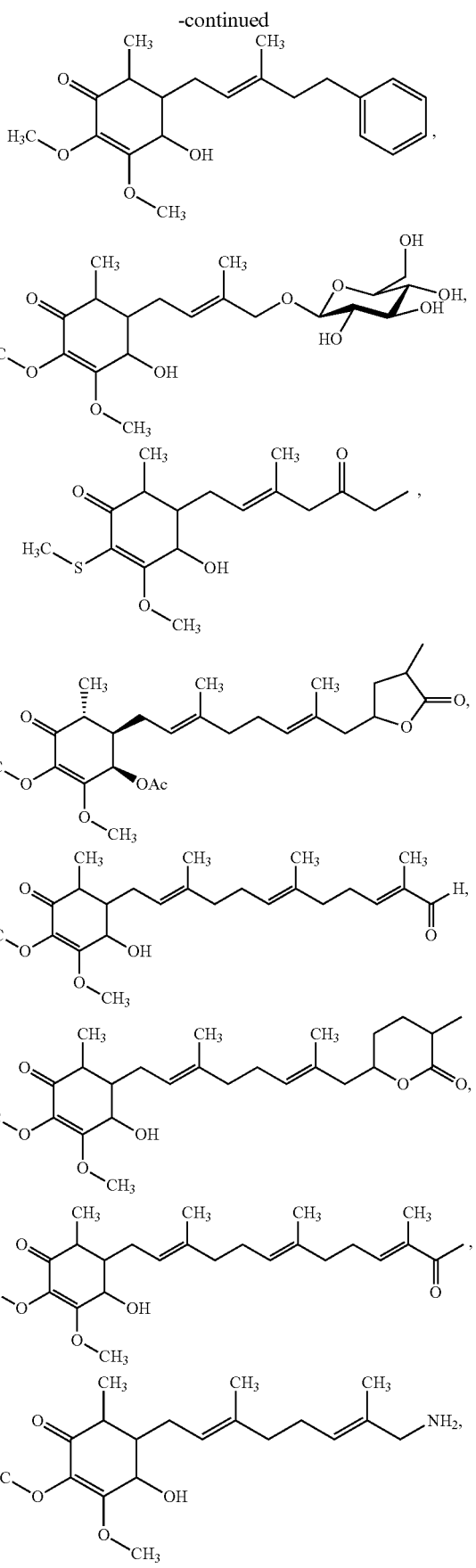

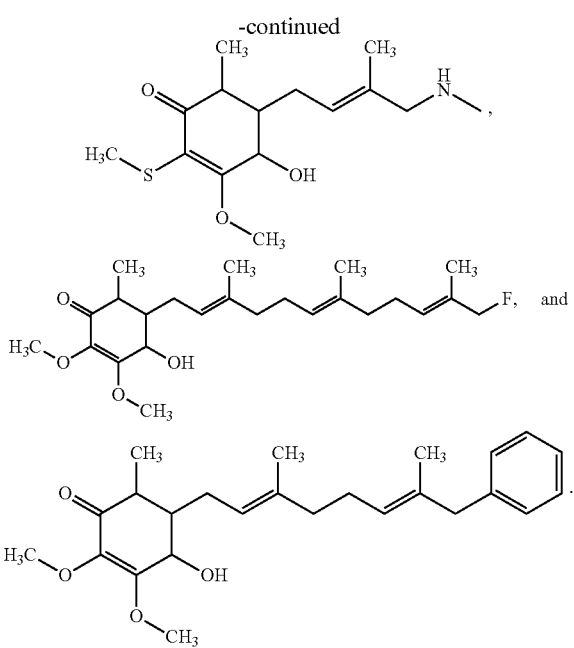
In certain embodiments, the compound is selected from group consisting of
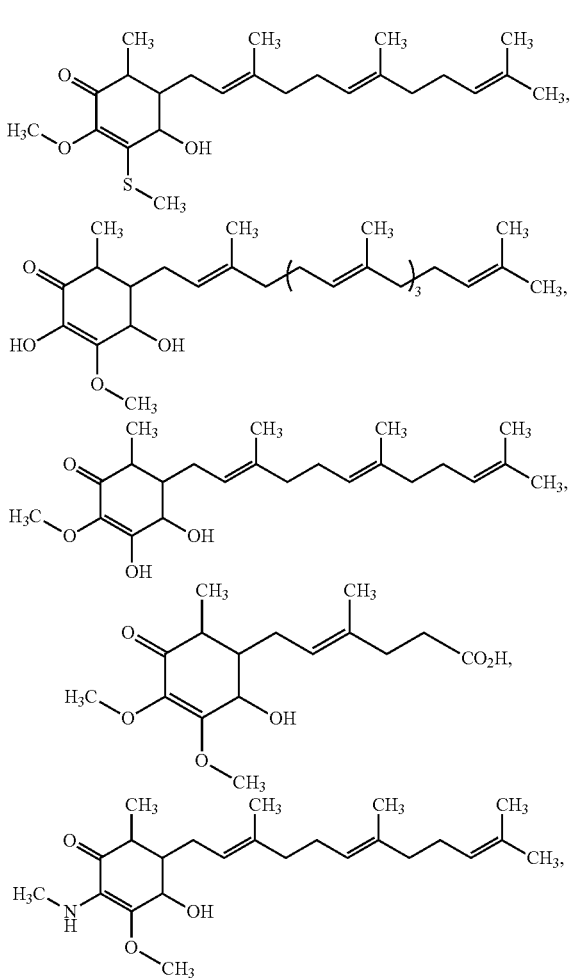
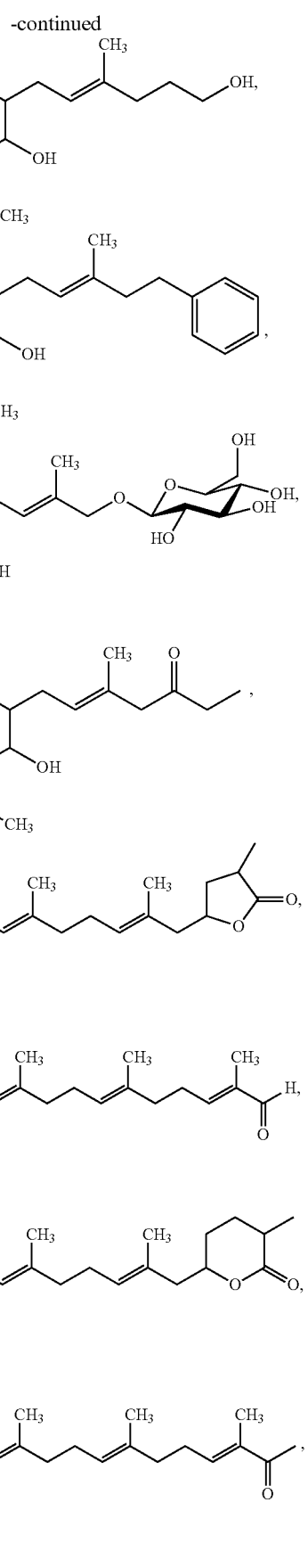

-continued

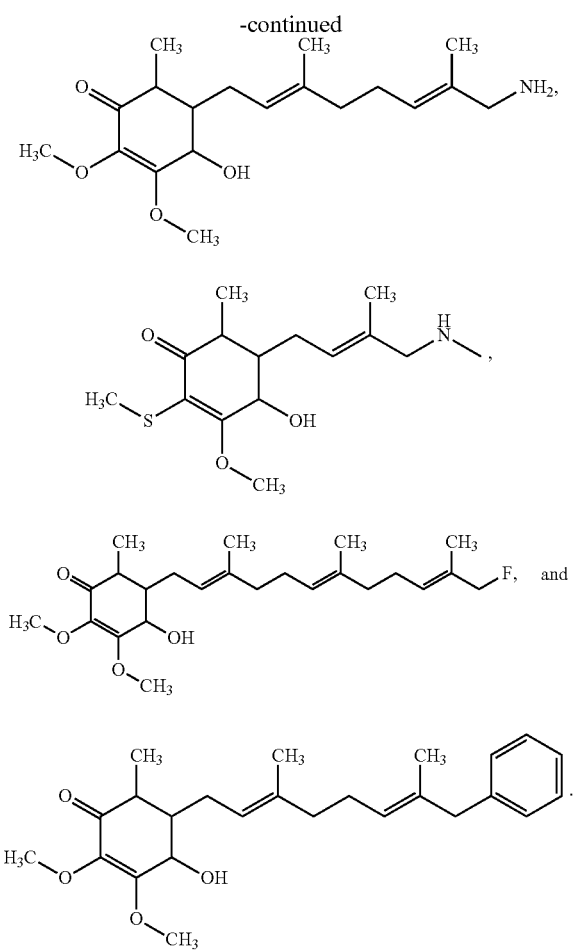

In some embodiments provide pharmaceutical compositions comprising a therapeutically effective amount of a cyclohexenone compound having the structure:

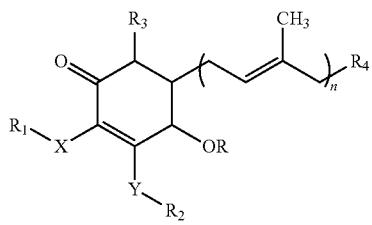

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof; and a pharmaceutically acceptable excipient.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are Obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, crosslinked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, hinders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorotluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,416,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example, polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (h) about 0.1.% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed, other agents do not have to be administered in the same pharmaceutical composition, and in some embodiments, because of different physical and chemical characteristics; are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other anti-cancer agents are intended to be covered. In some embodiments, examples of anti-cancer agents include, but are not limited to, the following: cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, other topoisomerase inhibitors (e.g., irinotecan, topotecan, camptothecin, etc.) or any derivative related agent of the foregoing.

The combinations of the cyclohexenone compounds and Other anti-cancer agents described herein encompass additional therapies and treatment regimens with other agents in some embodiments. Such additional therapies and treatment regimens can include another anti-cancer therapy in some embodiments. Alternatively, in other embodiments, additional therapies and treatment regimens include other agents used to treat adjunct conditions associated with the cancer or a side effect from such agent in the combination therapy. In further embodiments, adjuvants or enhancers are administered with a combination therapy described herein.

Additional anti-cancer therapies include chemotherapy, radiotherapy, immunotherapy, gene therapy, surgery or other therapies that are capable of negatively affecting cancer in a patient, such as for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

In some embodiments provide compositions for the treatment of lung cancer comprising a therapeutically effective amount of a cyclohexenone compound having the structure:

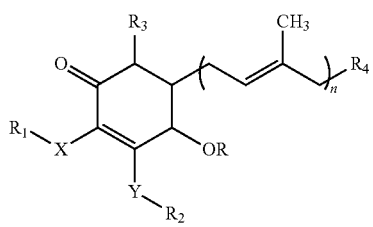

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and n=1-12; or a pharmaceutically acceptable salt, metabolite, solvate or prodrug
thereof; and one or more anti-cancer agents.

EXAMPLES

Example 1

Preparation of the Exemplary Cyclohexenone Compounds

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of Antrodia camphorate was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-triinethyldodeca-2,6-dienyl)-2,3-dimethoxy-6-methylcyclohex-2-enone with molecular weight of 408 (Molecular formula: $C_{24}H_{40}O_5$). $^1$H-NMR ($CDCl_3$) δ (ppm)=1.21, 1.36, 1.67, 1.71, 1.75, 1.94, 2.03, 2.07, 2.22, 2.25, 3.68, 4.05, 5.71 and 5.56. $^{13}$C-NMR ($CDCl_3$) δ(ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

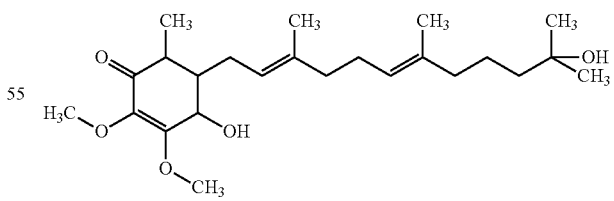

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methyleyclohex-2-enone with molecular weight of 422 ($C_{25}H_{42}O_5$). $^1$H-NMR (CDCl$_3$) δ(ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR (CDCl$_3$) δ(ppm): 12.31, 16.1, 16.12, 17.67, 24.44, 26.44, 26.74, 27.00, 37.81, 39.81, 40.27, 43.34, 49.00, 59.22, 60.59, 120.97, 123.84, 124.30, 135.92, 138.05, 160.45 and 197.12.

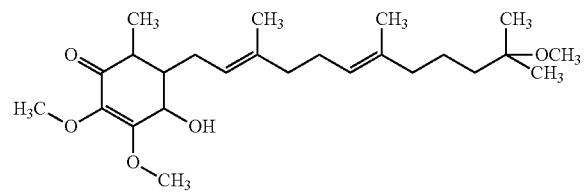

Compound 7: 4-hydroxy-2,3-dimethoxy-5-(11-methoxy-3,7,11-trimethyldodeca-2,6-dienyl)-6-methylcyclohex-2-enone The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR (CDCl$_3$) δ(ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ(ppm)=12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

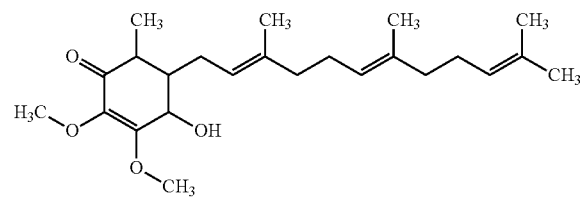

Compound 1: 4-hydroxy-2,3-dimethoxy-6-methyl-5-(3,7,11-trimethyldodeca-2,6,10-trienyl)cyclohex-2-enone Compound 6, a metabolite of compound 1, was obtained from urine samples of rats fed with Compound 1 in the animal study. Compound 6 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 4 which was determined as 3,4-dihydroxy-2-methoxy-6-methyl-5-(3,7,11-trimethyldodeca-2,6,10-trienyl)cyclohex-2-enone (molecular weight of 376, $C_{23}H_{36}O_4$), was obtained when compound 1 was under the condition of above 40° C. for 6 hours.

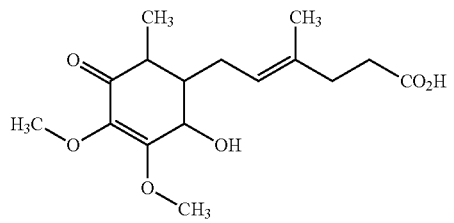

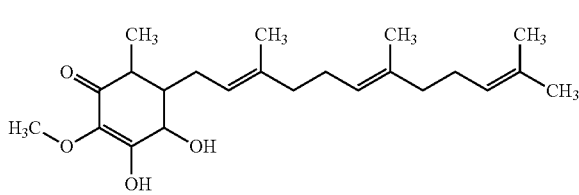

Alternatively, the exemplary compounds may be prepared from 4-hydroxy-2,3-dimethoxy-6-methylcyclohexa-2,5-dienone, or the like.

Similarly, other cyclohexenone compounds having the structure

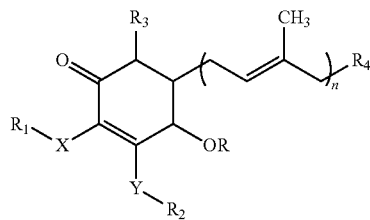

are isolated from *Antrodia camphorata* or prepared synthetically or semi-synthetically from the suitable starting materials. An ordinary skilled in the art would readily utilize appropriate conditions for such synthesis.

Example 2

In Vitro Survival Assay for Anti-Lung Cancer Effects

The NCI anti-cancer drug screen model was adopted to test anti-cancer effect of the exemplary compounds from Example 1. The isolated compound 1 from Example 1 was added into the culture media of human lung-cancer cells, A549, NCI-H460, CL1-0, CL1-5 or DMS 114, to test for tumor cell survival (either by MTT assay or colony formation assay). Compounds 4, 5, 6, and 7 were used in MTT assay against A549.

A549, CL1-0, and CL1-5 cells are human lung adenocarcinoma cell lines. CL1-0 cells are minimally invasive sublines with low migration. CL1-5 cell line, on the other hand, is highly invasive with high migration ability. The NCI-H460 cell line is derived from human large cell lung cancer, which is one of the major types of non-small cell lung carcinoma. DMS 114 is small cell lung cancer cell line, and was obtained from the American Type Culture Collection (Manassas, Va.).

MTT Assay

MTT assay is commonly used to determine cell proliferation, percent of viable cells, and cytotoxicity. MTT (3-[4,5-dimethylthiazol-2-yl]2,5-diphenyltetrazolium bromide) is a yellow dye, which can be absorbed by the living cells and be reduced to purplish blue formazan crystals by succinate tetrazolium reductase in mitochondria. Formazan formation can therefore be used to assess and determine the survival rate of cells.

A549, NCI-H460, CL1-0, CL1-5 and DMS 114 cells were suspended and cultured in 10% fetal bovine serum (Life Technologies Inc.) containing RPM1-1640 culture medium that also includes 1% penicillin and 1% streptomycin. Human bronchial epithelium cell line, BEAS-2B was used as a control. The BEAS-2B cell line was cultured in LHC-9 serum-free medium. All these cell lines were incubated under 5% $CO_2$, 37° C. for 24 hours. After cell proliferation, the cells were washed once with PBS, treated with the trypsin-EDTA, and then centrifuged at 1,200 rpm for 5 minutes to separate cells from supernatant. The cells were re-suspended in fresh culture medium (10 mL) and placed in 96 well plates.

Figure 1B:
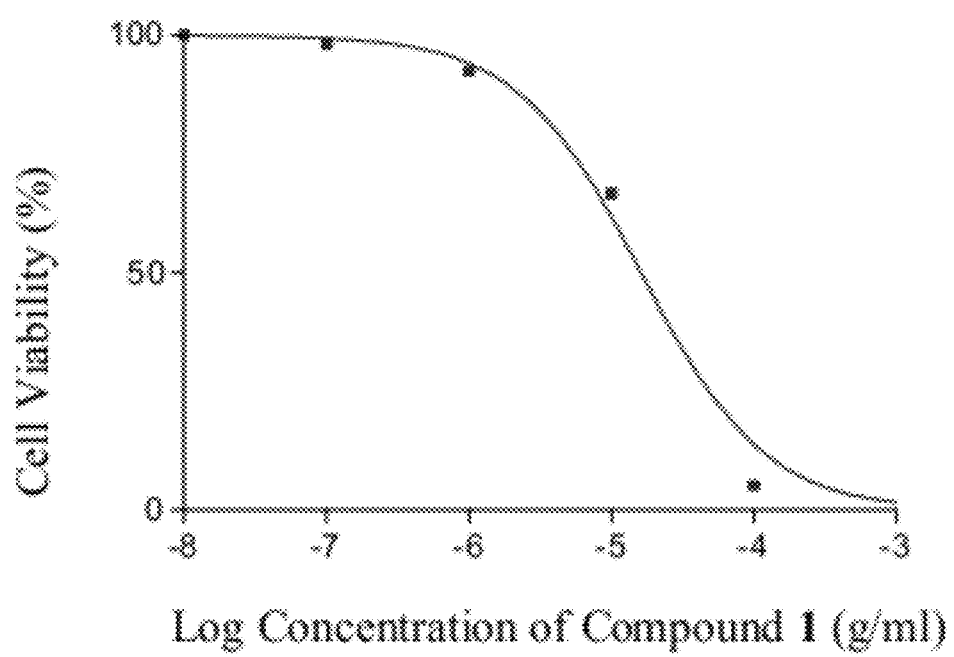

To each of the 96 well plates containing A549, NCI-H460, CL1-0, CL1-5, DMS 114 or BEAS-2B, 0.03, 0.1, 0.3, 1 and 3 µg/ml of compound 1 were add. The 96 well plates were incubated at 37° C., 5% $CO_2$ for 48 hours. Subsequently, in the dark environment to each well of the plates were added 2.5 mg/ml of MTT. The reaction was terminated by addition of 100 ul of lysis buffer after 4 hours. The survival rate of cells was calculated based on the measurement of absorption at the 570 nm wavelength by enzyme immunoassay analyzer. The results are shown in FIGS. 1A and 1B. The half maximal inhibitory concentration ($IC_{50}$) values of compound 1 on A549 and NCI-H460 are shown in Table 1 (A549: 0.45 µg/ml; NCI-11460: 0.82 µg/ml). Furthermore, FIG. 1B shows the higher concentrated of compound 1, the higher toxic to human small cell lung cancer cell line DMS 114. $IC_{50}$ of compound 1 against DMS 114 was 16.0 µM. These results indicated that the exemplary cyclohexenone compound 1 inhibits lung cancer cell growth and can be used for lung cancer treatment.

TABLE 1

Compound 1 in vitro Cell survival rate test results

| Cell lines | $IC_{50}$ (µg/ml) |
|---|---|
| A549 | 0.45 |
| NCI-H460 | 0.82 |

Similarly, 30, 10, 3, 1, 0.3, 0.1 and 0.03 µg/ml of Compound 6 were test on A549. Based on the results, $IC_{50}$ of compound 6 on A549 was determined (Table 2) to be 28.0 µM. These results indicated that compound 6 inhibits lung cancer cell growth and can be used for lung cancer treatment.

TABLE 2

Compound 6 in vitro Cell survival rate test results

| Cell lines | $IC_{50}$ (µg/ml) |
|---|---|
| A549 | 28 |

Similarly, 30, 10, 3, 1, 0.3, 0.1 and 0.03 µg/ml of Compound 5 and 7, respectively were used on A549. $IC_{50}$ of compounds 5 and 7 on A549 are shown in Table 3. $IC_{50}$ of compound 5 on A549 was 13.52 µg/ml. $IC_{50}$ of compound 7 on A549 was 10.52 µg/ml. These results indicate that compounds 5 and 7 inhibit lung cancer cell growth and can be used for lung cancer treatment.

TABLE 3

Compounds 5 and 7 in vitro Cell survival rate test results

| Compound | $IC_{50}$ (µg/ml) A549 |
|---|---|
| 5 | 13.52 |
| 7 | 10.52 |

Similarly, 30, 10, 3, 1, 0.3, 0.1 and 0.03 µg/ml of Compound 4 were tested against A549. $IC_{50}$ of compound 4 on A549 is shown in Table 4 (3.244 µg/ml). These results indicated that compound 4 inhibits lung cancer cell growth and can be used for lung cancer treatment.

TABLE 4

Compound 4 in vitro Cell survival rate test results

| Cell lines | $IC_{50}$ (µg/ml) |
|---|---|
| A549 | 3.244 |

In addition, FIG. 1A shows that the exemplary cyclohexenone compounds reduce cell viability rate on lung cancer cells but do not affect human bronchial epithelium cell line, BEAS-2B, which indicates low toxicity on normal cells.

Colony Formation Assay

The colony formation assay (CFA) is a gold standard for measuring the effects of cytotoxic agents on cancer cells in vitro. CFA determines cell survival fraction (SF). It is able to detect the cytotoxic effect of an agent, regardless of mechanism, as long as the agent affects the cell's reproductive ability to form progenies.

To each of the 6-well dishes containing A549, CL1-0 or CL1-5, 0.1, 0.3, 0.6, 1 and 3 µg/ml of compound 1 were add. Each of the 6-well dishes was mixed with 0.35% top agar containing RPMI-1640 cell culture medium and 0.7% lower agar containing RPMI-1640 cell couture medium and incubated at 37° C., 5% $CO_2$ for 14-21 days. The control dishes were prepared similarly without addition of compound 1. After formation of the cell colonies, 1 mg/ml of p-iodonitrot-erazolium violet (Sigma) was added to each dish and incubated at 37° C. in a 5% $CO_2$ incubator overnight to stain the cells. The results were observed under microscope and photographed. The number of 1 mm size colonies was calculated for each dish. See FIGS. 2A, 2B, 3A, 3B, 4A and 4B.

Figure 2A:
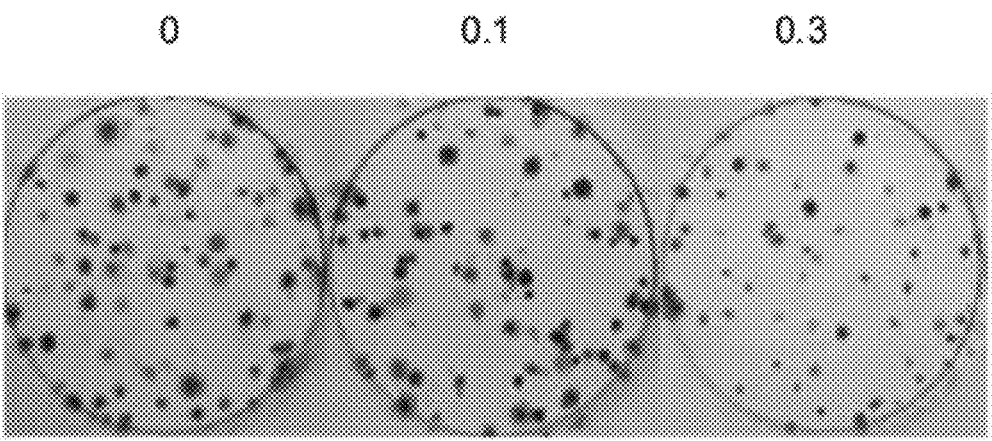
FIG. 2A-B show illustrative results of colony formation assay measuring the cytotoxic effect of the exemplary compound 1 on lung cancer cell line A549.
Figure 2A:
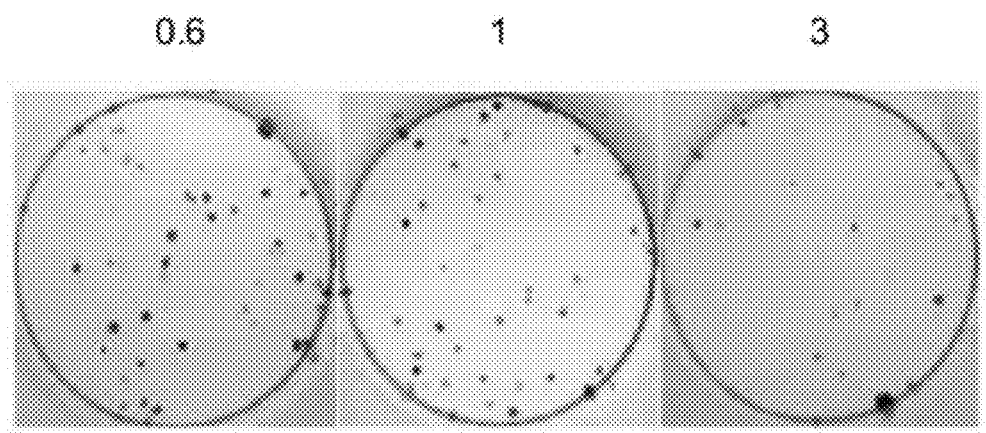
Figure 2B:
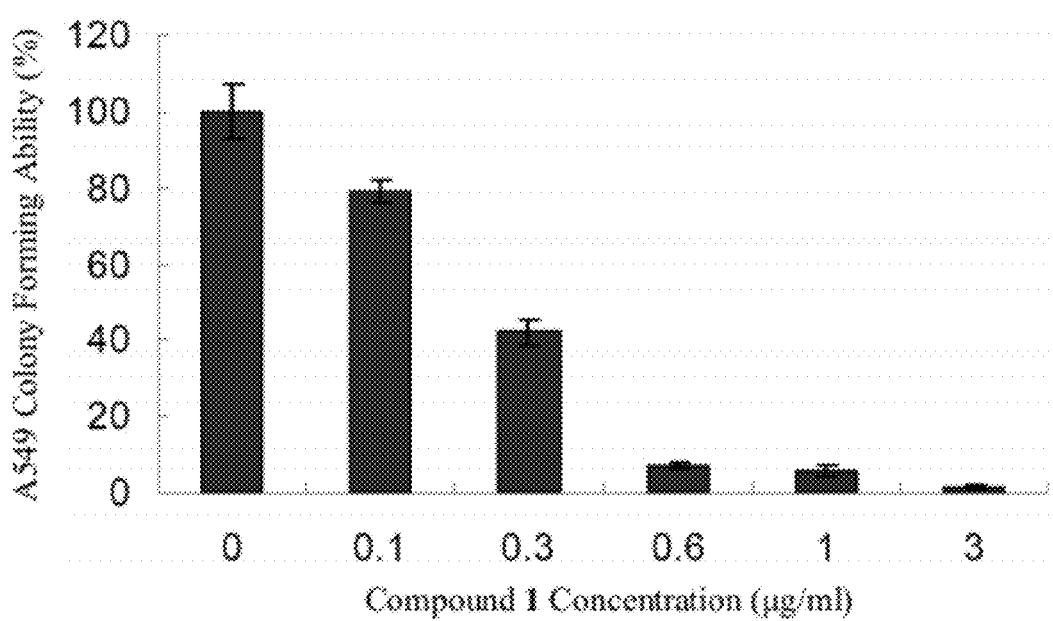
Figure 3A:
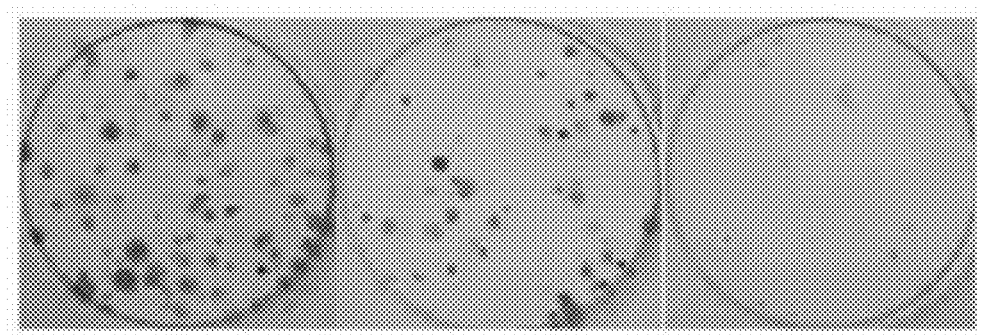
FIG. 3A-B show illustrative results of colony formation assay measuring the cytotoxic effect of the exemplary compound 1 on lung cancer cell line CL1-0.
Figure 3A:
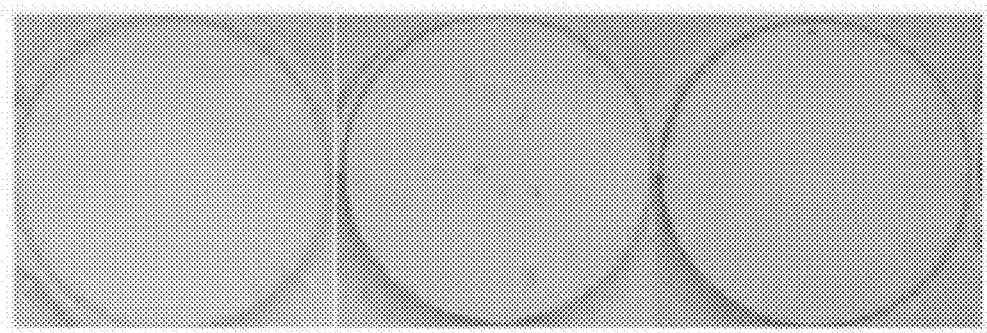
Figure 3B:
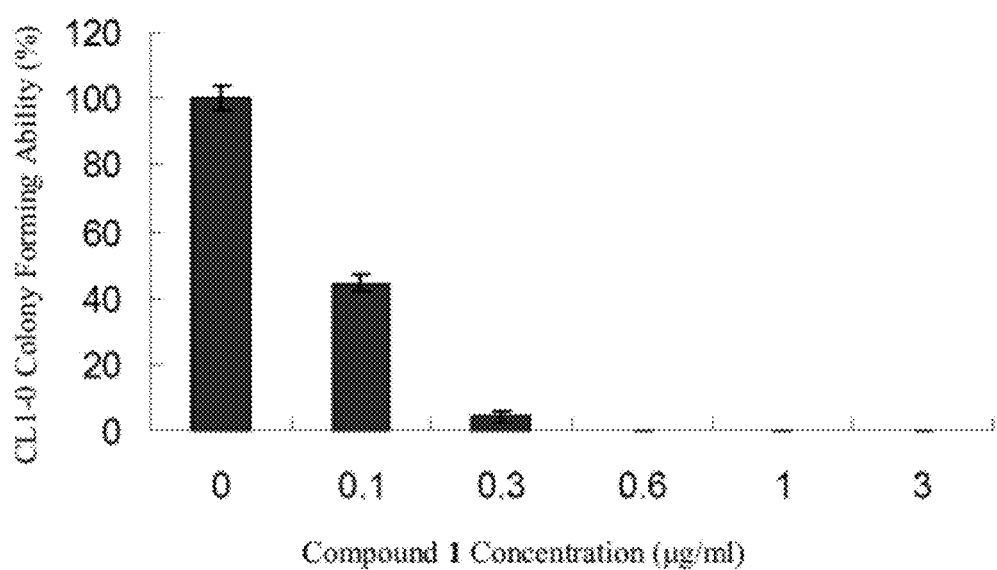
Figure 4A:
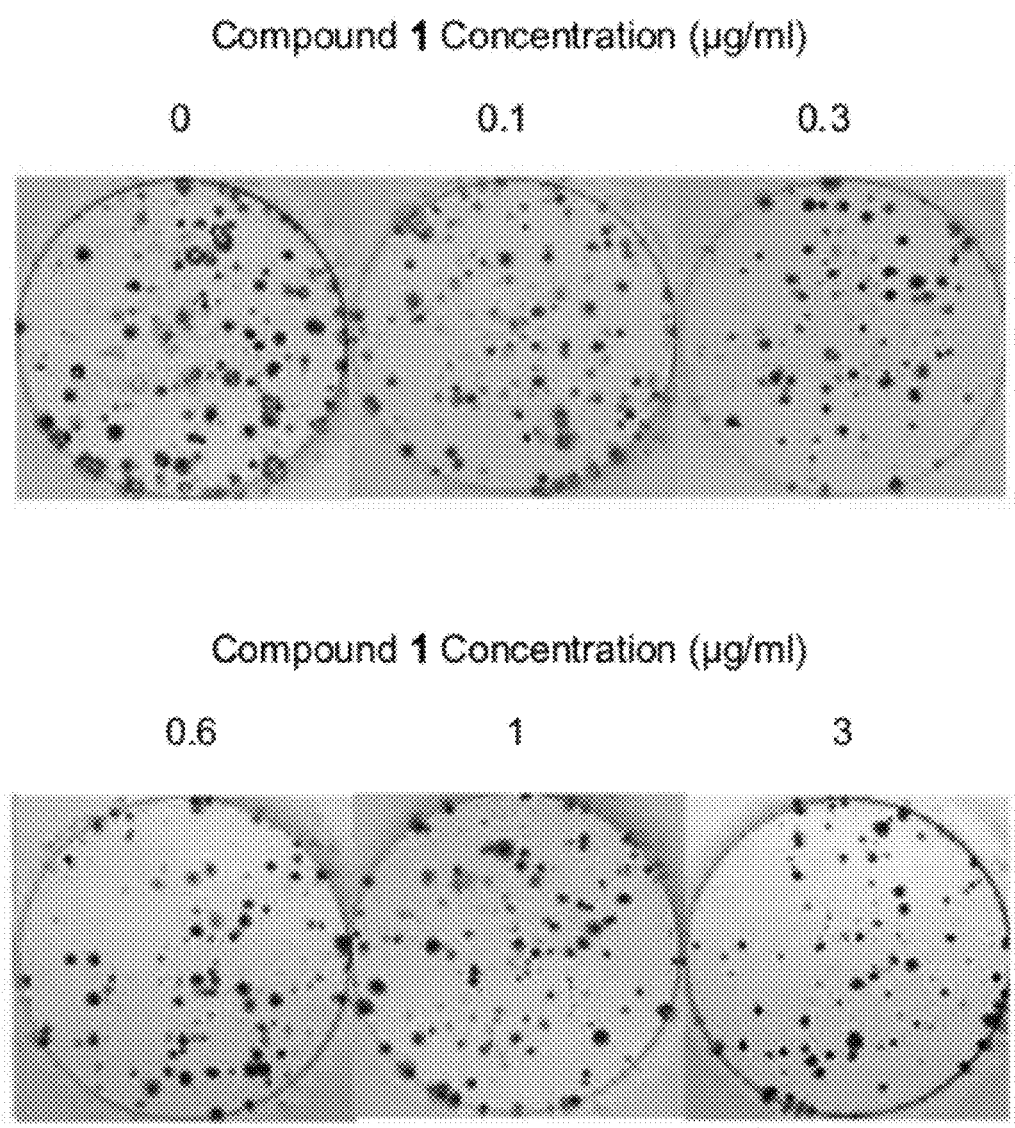
FIG. 4A-B show illustrative results of colony formation assay measuring the cytotoxic effect of the exemplary compound 1 on lung cancer cell line CL1-5.
Figure 4B:
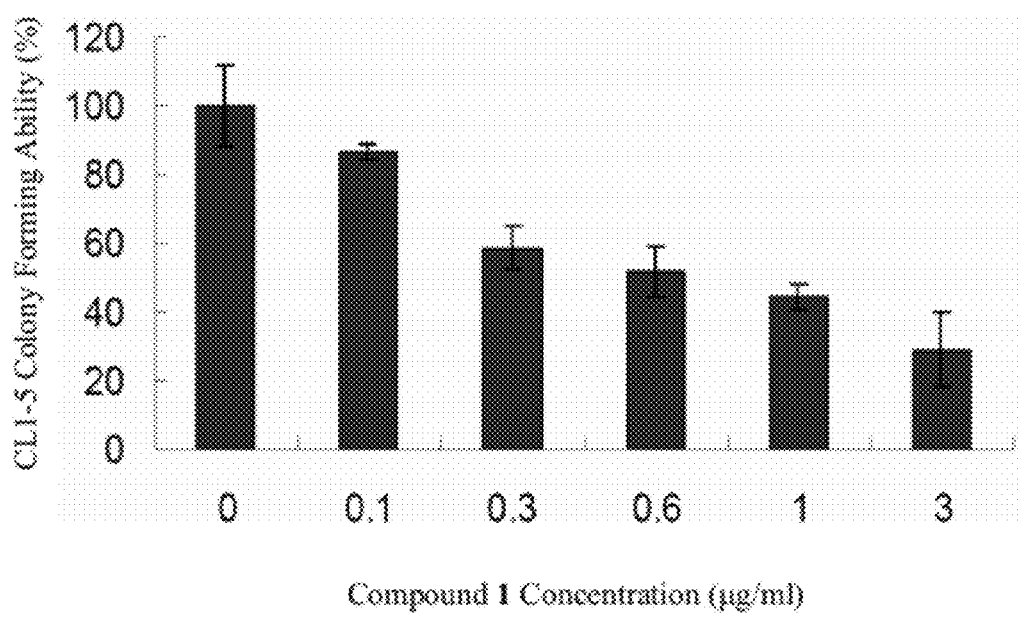

Referring to FIGS. 2A and 2B, when the exemplary compound 1 was used on lung cancer cell line A549, even in low dosing of 0.3 µg/ml, the invention cyclohexenone compound significantly reduced A549 cell colony forming ability. Similar effects were observed on CL1-0 and CL1-5 cell colony forming assays (See FIGS. 3A, 3B, 4A and 4B). These results indicate that the exemplary compound 1 inhibits lung cancer cell growth and can be used for lung cancer treatment.

Example 3

In Vitro Lung Cancer Cells Apoptosis Analysis

At different incubation time points (24, 48, and 72 hours), the compound 1 treated (0, 0.1, 0.3, 0.6, or 1 µg/ml) human lung cancer cell lines A549 and CL1-5 were collected. The cells were washed and fixated in 100% ethanol at 4° C. for one hour. After removal of ethanol, the cells were incubated with 2 mg/ml of RNase A at 37° C. for at least 30 minutes. The cells-were dyed with 50 µg/ml of propidium iodide at 4° C.

and analyzed by flow cytometry (Beckman Coulter PhoteomeLab™ PF 2D). The DNA contents of cells are shown in FIGS. 5 and 6.

Figure 5:
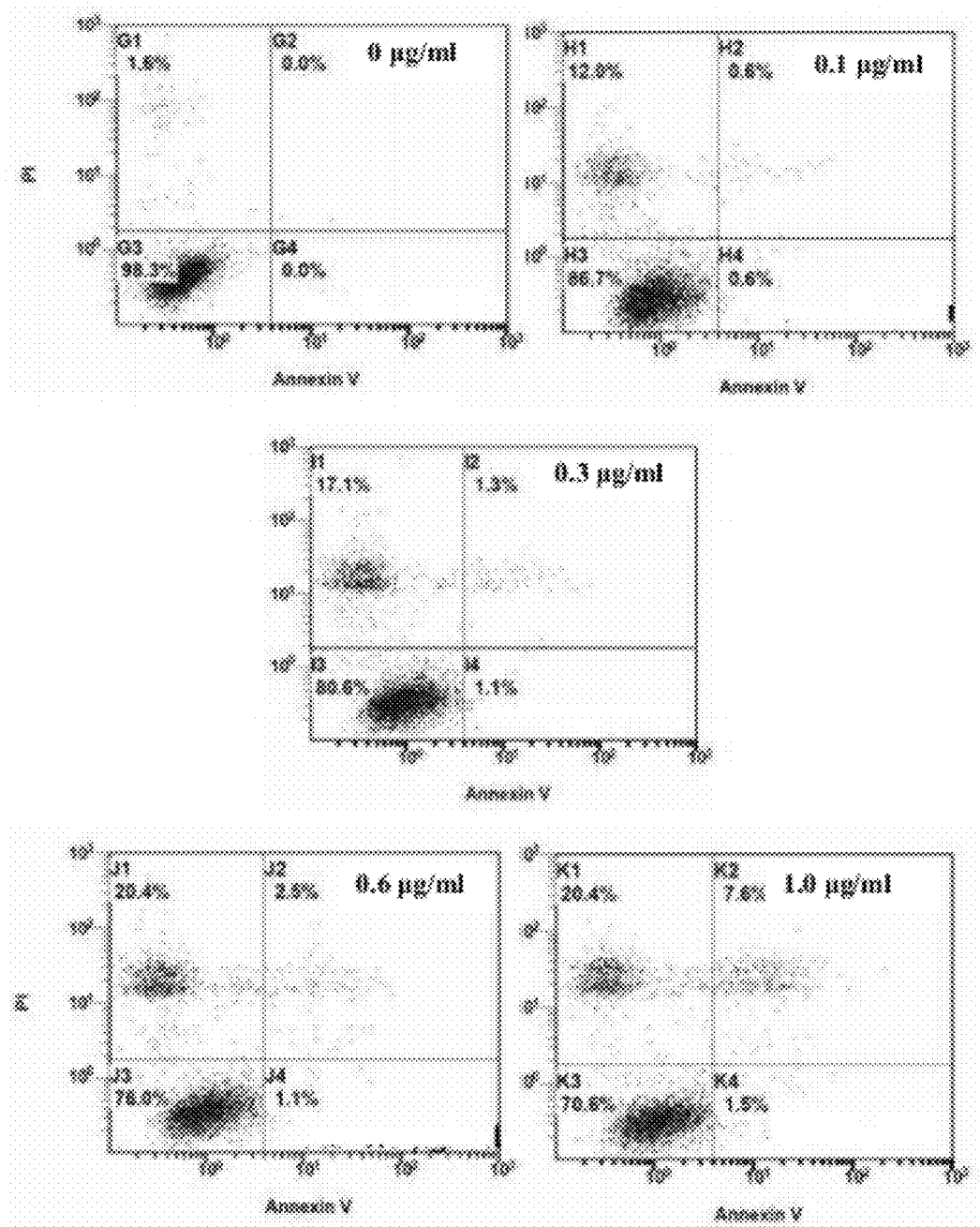
FIG. 5 shows illustrative results of apoptosis analysis by flow cytometry of lung cancer cell line A549.
Figure 6:
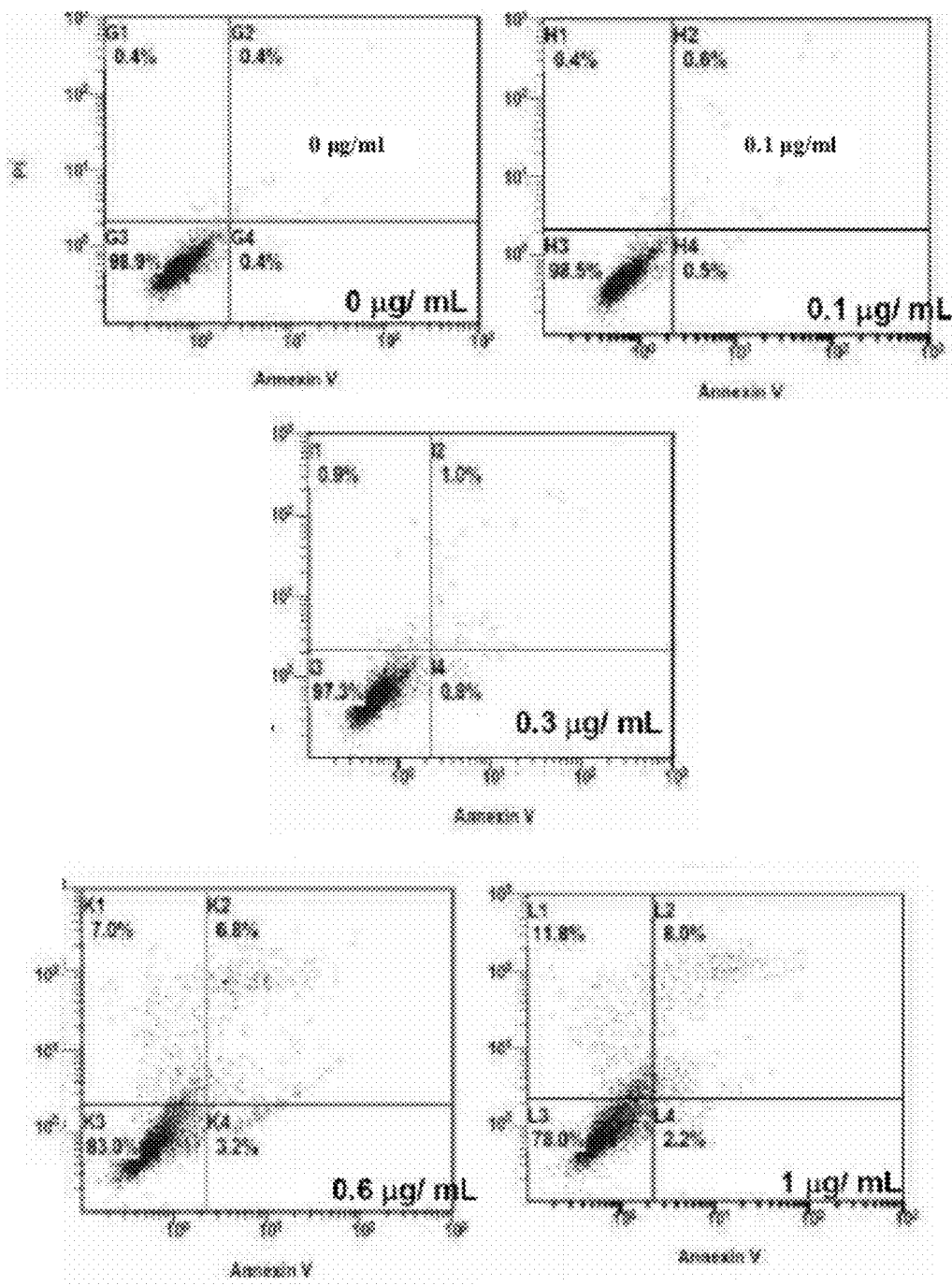
FIG. 6 shows illustrative results of apoptosis analysis by flow cytometry of lung cancer cell line CL1-5.

Referring to FIG. 5, the results show that A549 human lung cancer cell survival rate decreased after 48 hours treatment of the exemplary compound 1. The higher concentrated of compound 1, the more significant decrease of cell survival rate. This indicates the increase of cell apoptosis of human lung cancer cell A549. In FIG. 6, the results show that human lung cancer cell CL1-5 survival rate significantly decreased after 72 hours treatment, the higher concentrated of the exemplary compound 1, the higher cell apoptosis of CL1-5. These results show that the exemplary compounds increase human lung cancer cell apoptosis.

Example 4

In Vitro Lung Cancer Cell Migration and Invasion Analysis

In Vitro Cancer Cell Migration Assay

Figure 7:
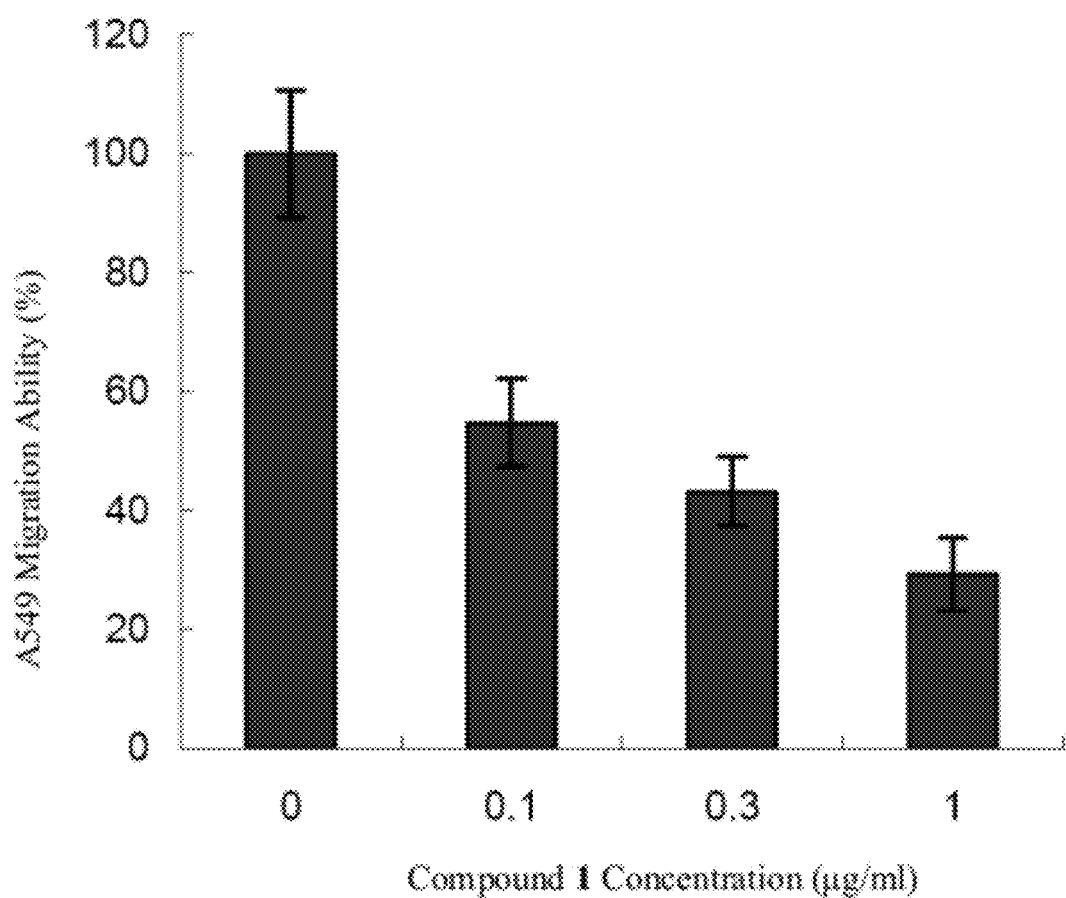
FIG. 7 shows illustrative results of the relative lung cancer cells A549 migration ability (expressed as a percentage) treated with the exemplary compound 1. The control (non-treated cells) has 100% migration ability.

To a 6-well dish were added compound 1 treated A549 cells (0.1, 0.3 or 1 μg/ml) that have cell density of $2\times10^5$. The cells with and without compound 1 treatment were incubated at 37° C., in a 5% carbon dioxide incubator to culture full and then washed with one time of PBS buffer. The single layer cells were scraped off by a rubber spatula and the resulted cells were washed with one time of PBS buffer. The cells were placed back to a 5% carbon dioxide cell incubator at 37° C. after addition of 2 ml culture medium. The cell migration was observed at 0, 12, 24, and 48 hours under microscope. The relative lung cancer cells migration ability (expressed as a percentage) was calculated and compared between the compound 1 treated cells with the control group. The results are shown in FIG. 7. The results show that human lung cancer cell A549 cell migration ability significantly decreased after the compound 1 treatment, the higher concentrated of the exemplary compound 1, the lower cell migration ability of A549. The results show that the exemplary cyclohexenone compounds effectively prevent lung cancer cell migration.

In Vitro Cancer Cell Invasion Assay

The analysis of cancer cell invasion ability is based on membrane invasion culture system (MICS) method. CL1-5, a highly invasive lung cancer cell line was used to optimize the invasion assay conditions.

Figure 8:
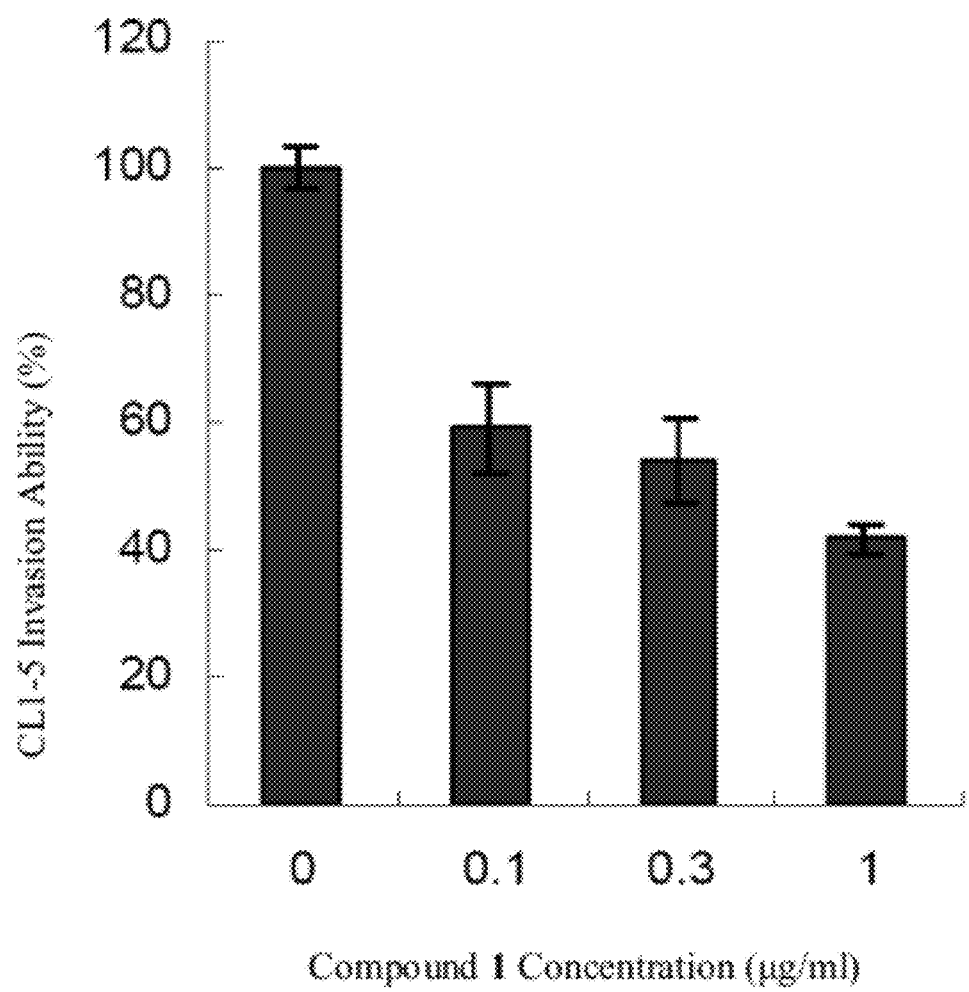
FIG. 8 shows illustrative results of the relative lung cancer cells CL1-5 invasion ability (expressed as a percentage) treated with the exemplary compound 1. The control (non-treated cells) has 100% invasion ability.

A 24-well dish containing 8 μm polycarbonate filters was soaked in PBS buffer and placed in a 5% carbon dioxide incubator at 37° C. overnight. To the upper chambers of the 24-well dish were covered with Matrigel diluted with 60 μl of 1:2 ratio of serum-free medium so the Matrigel was evenly spread and solidified in the inner layer of the upper chambers. To the lower chambers of the 24-well dish were added 600 μl of serum-free medium and then the upper chambers of the 24-well dish. To the upper champers of the 24-well dish were added untreated or compound 1 treated CL1-5 cells (0, 0.1, 0.3 or 1 μg/ml) that have cell density of $2\times10^5$. The dish was incubated in a 5% carbon dioxide incubator at 37° C. for 18 hours. Some cells from upper champers penetrated Matrigel and moved to lower champers. The medium and adhesion cells in the upper chambers were removed. The cells in the upper champers (on the back) were fixated with cold methanol for 15 min and then dyed with Giemza stain for at least one hour. The number of cells were observed and calculated under microscope that is corresponding to the relative lung cancer cells invasion ability (expressed as percentage). The results are shown in FIG. 8. The results show that cell invasion ability of human lung cancer cell line CL1-5 significantly decreased after treated with compound 1, the higher concentrated of the exemplary compound 1, the lower cell invasion ability of CL1-5. The result shows that the exemplary cyclohexenone compounds effectively prevent lung cancer cells invasion.

Example 5

Animal Tumorigenesis

Figure 9:
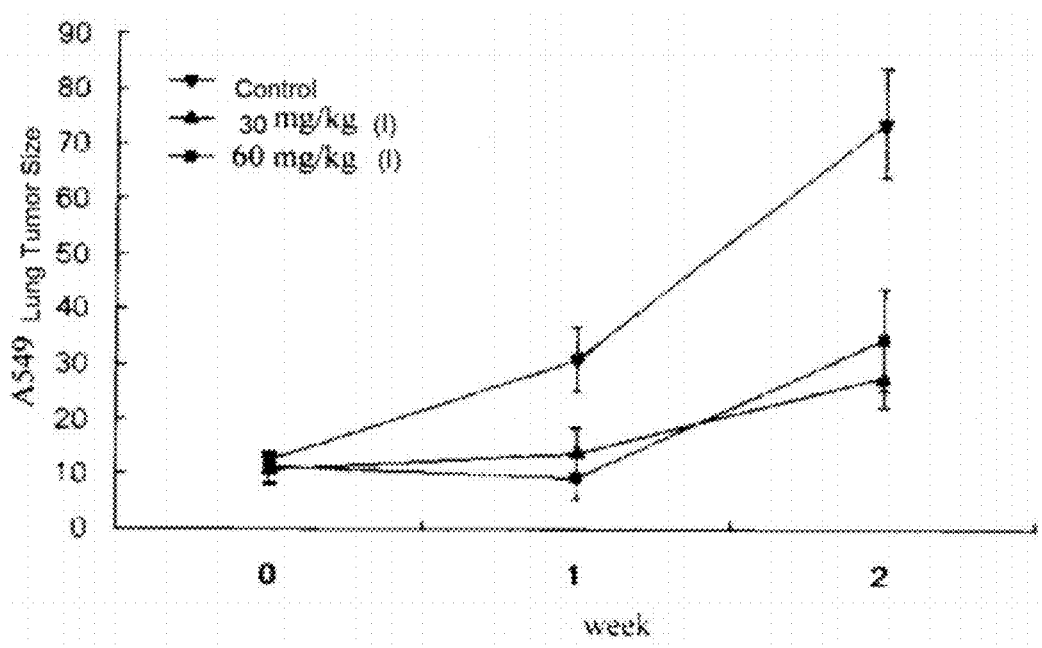
FIG. 9 shows illustrative results of animal tumorigenesis on 6-week-old SCID mice. The results show that the exemplary compound 1 effectively inhibits lung tumor growth.

Experiments described herein were performed on 6-week-old SCID mice. The fluorescent protein expressed (eGFP) lung cancer cell line A549 was prepared according to the known procedure. The A549-eGFP mice were injected subcutaneously on the back of each mouse with 2 ml of A549-eGFP cells (about $5\times0.10^6$ cells). Two groups of the mice were given compound 1 (30 mg/Kg and 60 mg/kg) for 7-14 days while the control group was fed corn oil only. The tumor size of each group of the mice was recorded and measured ($mm^3$) by a non-invasive 3D IVIS Imaging System. The results are shown in FIG. 9. The tumor size in control group grew rapidly, while the tumor size in the cyclohexenone compound 1 treated groups grew significantly smaller and slower than the control group. The results show that the invention cyclohexenone compounds effectively inhibit lung tumor growth in vivo.

Example 6

Drug Distribution in Organs Analysis

Experiments described herein were performed on CD-1 male mice (average weight 24±2 grams, provided by BioLasco, Taiwan). The mice were injected intravenously with a solution of compound 1 in 5% ethanol and 30% PEG400 (2 mg/Kg body weight). After 0.25, 0.5, 1, 2, 4 hours of the iv injection, 0.5 ml of blood was collected via cardiac puncture. The bloods were placed in a centrifuge tube containing K-EDTA and centrifuged for 15 min at 4° C. under 1500 g to produce supernatants (plasma sample). At the same time points, lung, kidney, small intestine and large intestine of the mice were collected and preserved at −70° C. for similar analysis.

Figure 10:
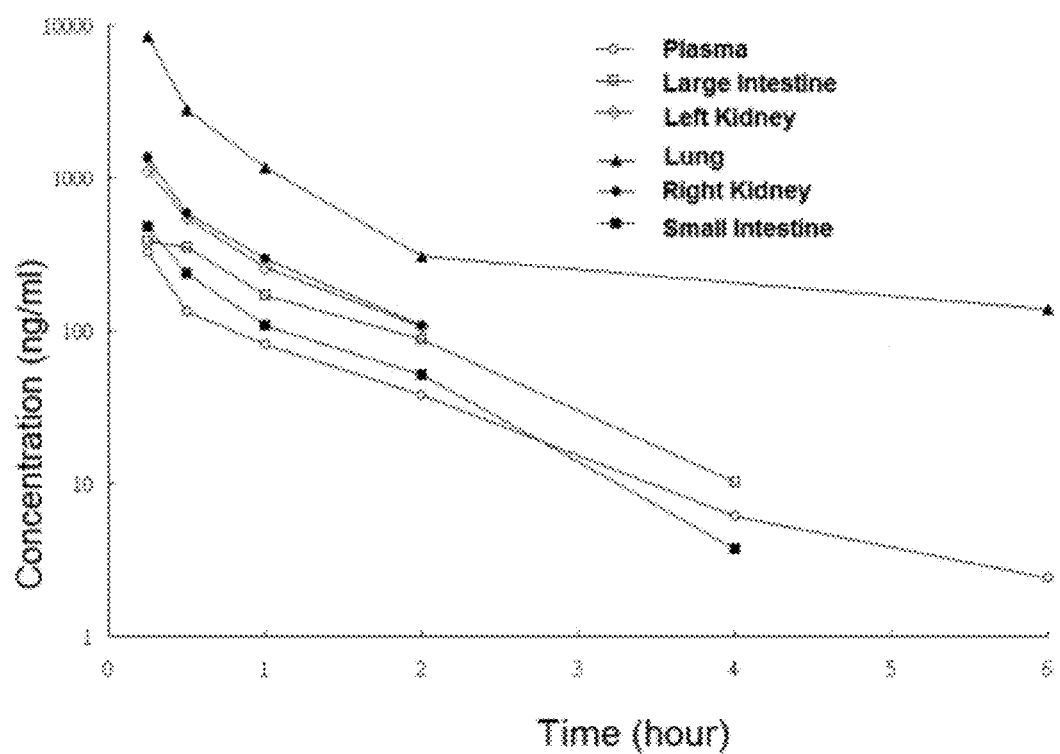
FIG. 10 shows illustrative results of drug distribution in mice. The exemplary compound 1 was found in lung with significantly higher concentration than other organs.

The concentration of compound 1 in various organ samples (i.e., plasma, large intestine, left kidney, lung, right kidney and small intestine) were analyzed by LC/MS/MS spectrometer (Waters Alliance 2790 LC and Micromass Quattro Ultima). For example, plasma sample was mixed with acetonitrile and then centrifuged to prepare supernatant that was analyzed by LC/MS/MS. The pharmacokinetic parameters were obtained by WinNonlin™ software by non-compartment method. The results are shown in FIG. 10. The exemplary compound 1 was found in lung with significantly higher concentration than other organs. The organ distribution analysis shows that the exemplary cyclohexenone compounds are suitable fir lung cancer treatment.

Example 7

Clinical Study in Non-Small Cell Lung Carcinoma

The purpose of the study is to evaluate if Compound 1 has an effect on the tumors (e.g., non-small cell lung tumors), how long the effect continues, if the patients receiving Compound 1 will live longer. Especially, If Compound 1 has an effect on the quality of life of patients with non-small cell lung cancer; If Compound 1 helps to slow the worsening of non-small cell lung cancer; If Compound 1 prevents the growth of, or shrinks non-small cell lung tumors and/or their metastases.

Study type: Interventional. Study design: allocation: non-randomized; control: uncontrolled; endpoint classification: safety and efficacy study; intervention model: single group assignment; masking: open label; primary purpose: treatment.

Primary Outcome Measures:

Anti-cancer Activity (e.g., percentage of patients with confirmed complete responses (CR) and partial responses (PR) per RECIST (Response Evaluation Criteria in Solid Tumors).

Secondary Outcome Measures:

Safety of Compound 1 in dose-escalation (adverse events and serious adverse events) is measured. Timeframe is one year.

Criteria in Patients with Stage IV Non-Small Cell Lung Carcinoma (NSCLC)

Time Frame: First patient first treatment until date for last data collection for efficacy for a study period up to 52 weeks. Tumor assessed per RECIST at baseline (BL), every 8 weeks during treatment and at end of treatment.

CR-Disappearance of Clinical/Radiological Tumor Evidence (Target/Nontarget)

PR←=30% decrease in sum longest diameter (LD) of target lesions from BL sum LD. Stable disease (SD)-no shrinkage for PR nor increase for PD. Progressive disease (PD) measurement proven←=20% increase in sum LD of lesions from smallest sum LD since start or new lesions. Progression by clinical judgment←clinically meaningful cancer-related deterioration as judged by the investigator.

The clinical trial will enroll a number of suitable patients (e.g. 50) with age>=20 years old.

Arms

Compound 1: Experimental. Intervention: Drug: Compound 1.

Assigned Intervention

Drug: Compound 1. Dosage form: 100 mg capsule bid×28 day cycles (Continuous treatment for a maximum of 2 years; potential for compassionate use and long term survival follow-up post drug discontinuation).

The results show that patients who take Compound 1 show improvement over lung cancer. The patients receiving Compound 1 live longer with better quality of life. Compound 1 helps to slow the worsening of non-small cell lung cancer. The results also indicate that Compound 1 prevents the growth of, and shrinks non-small cell lung tumors and/or their metastases. These results are clinically significant, and thus the preliminary results clearly favor Compound 1 for the treatment of lung cancer. The invention cyclohexenone compounds are therefore promising candidates for improvement of chemotherapy results in lung cancer.

Example 8

Parenteral Formulation

To prepare a parenteral pharmaceutical composition suitable, for administration by injection, 100 mg of a compound or its salt described herein is dissolved in DMSO and then mixed with 10 mL of 0.9% sterile saline. The mixture is incorporated into a dosage unit form suitable for administration by injection.

Example 9

Oral Formulation

To prepare a pharmaceutical composition for oral delivery, 100 mg of an exemplary Compound 1 was mixed with 100 mg of corn oil. The mixture was incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 10

Sublingual (Hard Lozenge) Formulation

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 11

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 12

Rectal Gel Formulation

To prepare a pharmaceutical composition for rectal delivery, 100 mg of a compound described herein is mixed with 25 g of methylcellulose (1500 mPa), 100 mg of methylparapen, 5 g of glycerin and 100 mL of purified water. The resulting gel mixture is then incorporated into rectal delivery units, such as syringes, which are suitable for rectal administration.

Example 13

Topical Gel Composition

To prepare a pharmaceutical topical gel composition, 100 mg of a compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 14

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for the treatment of lung cancer comprising administering to a subject a therapeutically effective amount of a cyclohexenone compound having the structure:

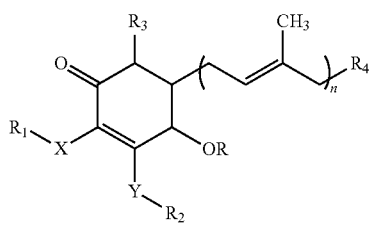

wherein each of X and Y independently is oxygen, $NR_5$ or sulfur;
R is a hydrogen or $C(=O)C_1\text{-}C_8$alkyl;
each of $R_1$, $R_2$ and $R_3$ independently is a hydrogen, methyl or $(CH_2)_m\text{—}CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8$alkyl, $C_2\text{-}C_8$alkenyl, $C_2\text{-}C_8$alkynyl, aryl, glucosyl, wherein 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;
each of $R_5$ and $R_6$ is independently a hydrogen or $C_1\text{-}C_8$alkyl;
$R_7$ is a $C_1\text{-}C_8$alkyl, $OR_5$ or $NR_5R_6$;
m=1-12; and
n=1-12; or a pharmaceutically acceptable salt, metabolite, solvate or prodrug thereof.

2. The method according to claim 1, wherein said method reduces lung cancer tumor size or tumor volume.

3. The method according to claim 1, wherein said method decreases lung cancer tumor growth rate.

4. The method according to claim 1, wherein said lung cancer is adenocarcinoma lung cancer.

5. The method according to claim 1, wherein said lung cancer is small cell lung cancer.

6. The method according to claim 1, wherein said lung cancer is non-small cell lung cancer.

7. The method according to claim 1, wherein said cyclohexenone compound induces cell death in said lung cancer.

8. The method according to claim 7, wherein said cell death is apoptosis.

9. The method according to claim 1, wherein said cyclohexenone compound, or a pharmaceutically acceptable salt, metabolite, solvate or prodrug thereof, is administered parenterally or intravenously.

10. The method according to claim 1, wherein said cyclohexenone compound, or a pharmaceutically acceptable salt, metabolite, solvate or prodrug thereof, is administered by injection.

11. The method according to claim 1, wherein said cyclohexenone compound, or a pharmaceutically acceptable salt, metabolite, solvate or prodrug thereof, is administered orally.

12. The method according to claim 1, wherein said subject is human.

13. The method of claim 1, wherein R is a hydrogen or $C(=O)CH_3$.

14. The method of claim 1, wherein $R_1$ is a hydrogen or methyl.

15. The method of claim 1, wherein $R_2$ is a hydrogen or methyl.

16. The method of claim 1, wherein $R_4$ is $CH_2CH=C(CH_3)_2$.

17. The method of claim 1, wherein said compound is

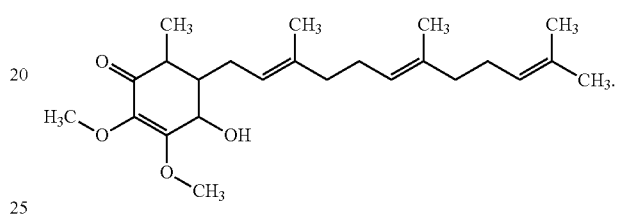

18. A method of treating a cell proliferative disorder of the lung, comprising administering to a subject in need a therapeutically effective amount of a cyclohexenone compound having the structure:

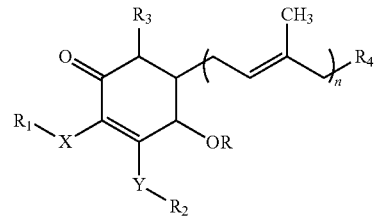

wherein each of X and Y independently is oxygen, $NR_5$ or sulfur;
R is a hydrogen or $C(=O)C_1\text{-}C_8$alkyl;
each of $R_1$, $R_2$ and $R_3$ independently is a hydrogen, methyl or $(CH_2)_m\text{—}CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8$alkyl, $C_2\text{-}C_8$alkenyl, $C_2\text{-}C_8$alkynyl, aryl, glucosyl, wherein 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;
each of $R_5$ and $R_6$ is independently a hydrogen or $C_1\text{-}C_8$alkyl;
$R_7$ is a $C_1\text{-}C_8$alkyl, $OR_5$ or $NR_5R_6$;
m=1-12; and
n=1-12; or a pharmaceutically acceptable salt, metabolite, solvate or prodrug thereof,
wherein said cell proliferative disorder of the lung is treated.

19. The method according to claim 18, wherein said cell proliferative disorder of the lung is lung cancer or a precancerous condition of the lung.

20. The method according to claim 18, wherein said cell proliferative disorder of the lung is hyperplasia or metaplasia of the lung.

21. A method for inhibiting lung cancer cells comprising contacting said cancer cells a therapeutically effective amount of a cyclohexenone compound having the structure:

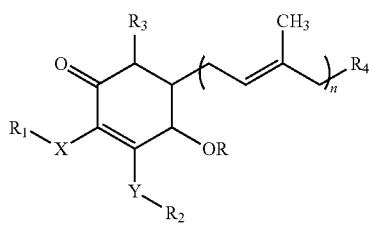

wherein each of X and Y independently is oxygen, $NR_5$ or sulfur;

R is a hydrogen or $C(=O)C_1\text{-}C_8\text{alkyl}$;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8\text{alkyl}$, $C_2\text{-}C_8\text{alkenyl}$, $C_2\text{-}C_8\text{alkynyl}$, aryl, glucosyl, wherein 5 or 6-membered lactone, $C_1\text{-}C_8\text{alkyl}$, $C_2\text{-}C_8\text{alkenyl}$, $C_2\text{-}C_8\text{alkynyl}$, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8\text{alkyl}$;

$R_7$ is a $C_1\text{-}C_8\text{alkyl}$, $OR_5$ or $NR_5R_6$;

m=1-12; and n=1-12; or a pharmaceutically acceptable salt, metabolite, solvate or prodrug thereof.

22. The method of claim 21, said lung cancer cells comprising non-small cell, small cell, or adenocarcinoma cell lung cancer cells.

23. The method of claim 21, wherein said lung cancer cells are human lung cancer cells.

24. The method of claim 21, wherein said cyclohexenone compound inhibits migration of the lung cancer cells.

25. The method of claim 21, wherein said cyclohexenone compound inhibits invasion of the lung cancer cells.

* * * * *